United States Patent
Görz et al.

(10) Patent No.: US 12,251,244 B2
(45) Date of Patent: Mar. 18, 2025

(54) MESH TRAY LID FOR MESH STERILIZING TRAY AND MESH STERILIZING TRAY SYSTEM

(71) Applicant: Aesculap AG, Tuttlingen (DE)

(72) Inventors: Dennis Görz, Tuttlingen (DE); Bianca Rosin, Tuttlingen (DE); Eva Streit, Bodman-Ludwigshafen (DE); Timo Knittel, Wurmlingen (DE); Matthias Henke, Fridingen (DE)

(73) Assignee: Aesculap AG, Tuttlingen (DE)

( * ) Notice: Subject to any disclaimer, the term of this patent is extended or adjusted under 35 U.S.C. 154(b) by 889 days.

(21) Appl. No.: 17/262,260

(22) PCT Filed: Jul. 18, 2019

(86) PCT No.: PCT/EP2019/069427
§ 371 (c)(1),
(2) Date: Jan. 22, 2021

(87) PCT Pub. No.: WO2020/020750
PCT Pub. Date: Jan. 30, 2020

(65) Prior Publication Data
US 2021/0259797 A1  Aug. 26, 2021

(30) Foreign Application Priority Data

Jul. 25, 2018 (DE) ...................... 10 2018 212 430.2
Nov. 30, 2018 (DE) ...................... 10 2018 130 542.7

(51) Int. Cl.
*A61B 50/33* (2016.01)
*A61B 50/00* (2016.01)
(Continued)

(52) U.S. Cl.
CPC ................ *A61B 50/33* (2016.02); *A61L 2/07* (2013.01); *A61L 2/26* (2013.01);
(Continued)

(58) Field of Classification Search
CPC .............. A61B 50/33; A61B 2050/007; A61B 2050/0067; A61B 2050/0083;
(Continued)

(56) References Cited

U.S. PATENT DOCUMENTS 5,065,885 A  11/1991  Scaroni
5,732,821 A  3/1998  Stone et al.
(Continued)

FOREIGN PATENT DOCUMENTS

CA  2676321 A1 *  3/2010  ............. A61B 50/20
CN  2316851  5/1999
(Continued)

OTHER PUBLICATIONS

Office Action received in Chinese Application No. 201980049098.0 dated Jul. 5, 2022, with translation, 19 pages.
(Continued)

*Primary Examiner* — Rafael A Ortiz
(74) *Attorney, Agent, or Firm* — Christopher A. Rothe; CM Law

(57) ABSTRACT

A mesh sterilizing tray system and mesh tray lid for a mesh sterilizing tray. The mesh tray lid includes a substantially rectangular plate-like or grid-like basic form which defines an outer side which, when being placed on the mesh sterilizing tray, faces away from the mesh sterilizing tray. A respective detent and/or snap-in device, which is designed for receiving a rod-shaped bar positively and/or in a force-fit manner from a direction substantially perpendicular to the outer side, is formed on two opposite edge portions on the outer side of the mesh tray lid.

11 Claims, 3 Drawing Sheets

Figure 1:
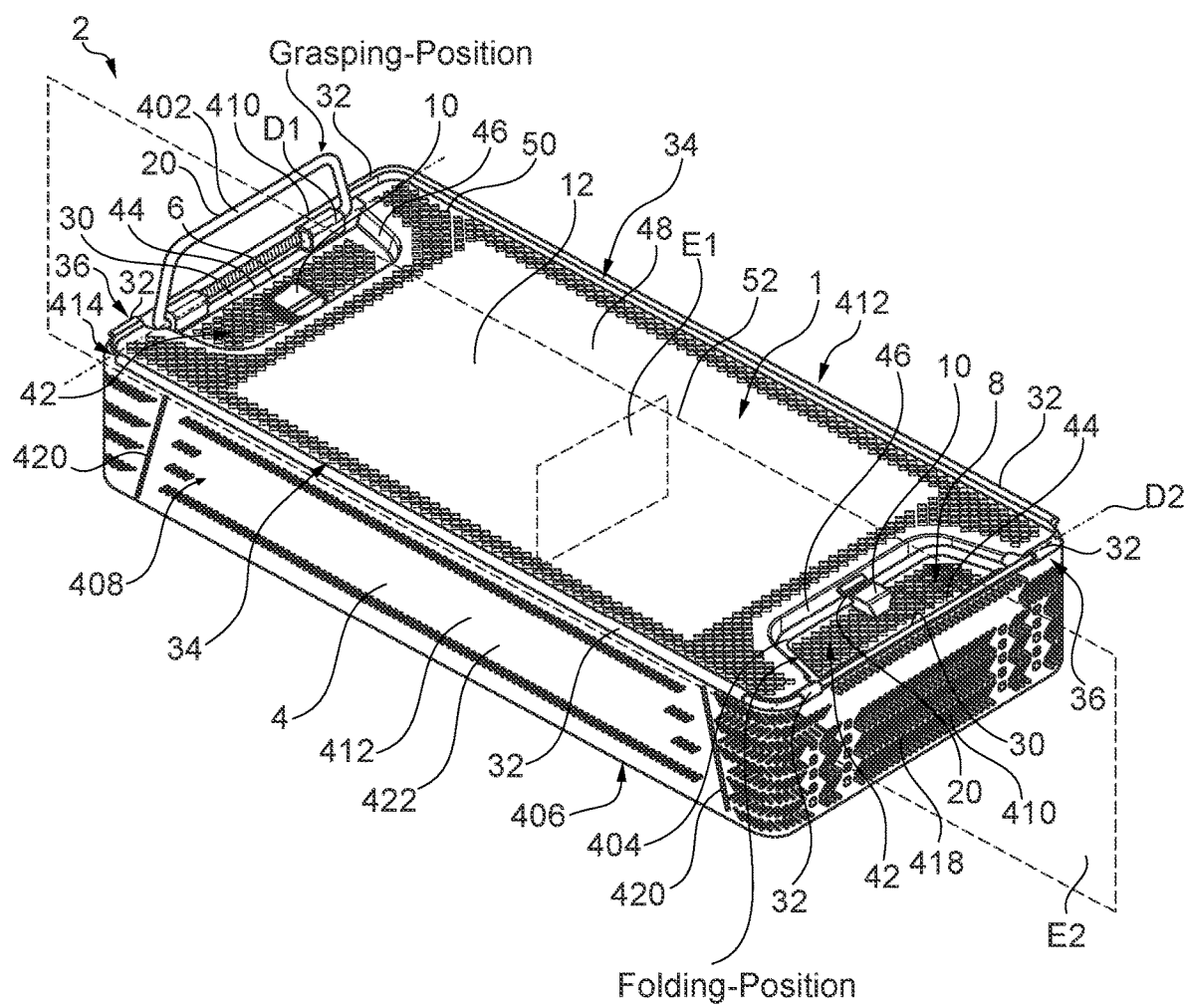

(51) Int. Cl.
*A61B 50/34* (2016.01)
*A61L 2/07* (2006.01)
*A61L 2/26* (2006.01)

(52) U.S. Cl.
CPC . *A61B 2050/007* (2016.02); *A61B 2050/0083* (2016.02); *A61B 50/34* (2016.02); *A61L 2202/182* (2013.01)

(58) Field of Classification Search
CPC ... A61B 2050/0082; A61B 50/34; A61L 2/26; A61L 2202/182
USPC ....... 206/577, 210, 223, 270, 571, 363–366, 206/368–370, 557, 478, 1.5; 24/323, 324, 24/326, 327, 336, 337, 346, 456, 482, 24/530; 220/244
See application file for complete search history.

(56) References Cited

U.S. PATENT DOCUMENTS

| | | | |
|---|---|---|---|
| 5,904,269 | A | 5/1999 | Wolff |
| 6,116,452 | A | 9/2000 | Hamel et al. |
| 6,991,108 | B1 | 1/2006 | Rorato et al. |
| 7,905,353 | B2* | 3/2011 | Baker .................... B65D 1/28 206/370 |
| 8,091,184 | B2* | 1/2012 | Santin .................. B60N 2/5825 24/339 |
| 10,856,950 | B2 | 12/2020 | Schuster et al. |
| 2006/0118445 | A1* | 6/2006 | Faust, III ............... A61B 50/30 206/363 |
| 2006/0213794 | A1* | 9/2006 | Foreman .................. A61L 2/26 206/439 |
| 2006/0266666 | A1* | 11/2006 | Bettenhausen ........... A61L 2/18 206/370 |
| 2007/0212277 | A1* | 9/2007 | Riley .................... A61B 50/34 206/370 |
| 2008/0000899 | A1 | 1/2008 | Baker et al. |
| 2008/0190932 | A1* | 8/2008 | Orr .................... B65D 21/0228 220/318 |
| 2009/0146032 | A1* | 6/2009 | Bettenhausen ........ A61B 50/30 248/220.31 |
| 2013/0175276 | A1 | 7/2013 | Gleichauf et al. |
| 2014/0069841 | A1* | 3/2014 | Pizzato .................. B25H 3/026 206/570 |
| 2016/0073745 | A1* | 3/2016 | Moreau .................. F16M 13/04 24/336 |
| 2018/0044059 | A1* | 2/2018 | Brunner .................. B25H 3/02 |

FOREIGN PATENT DOCUMENTS

| | | | |
|---|---|---|---|
| CN | 114599307 A | 6/2022 | |
| DE | 9311451 U1 | 10/1993 | |
| DE | 102010050919 A1 | 5/2012 | |
| DE | 102016118083 A1 | 3/2018 | |
| WO | 0178619 A1 | 10/2001 | |
| WO | 0217976 A1 | 3/2002 | |
| WO | WO-2008100858 A2 * | 8/2008 | ......... B65D 21/0228 |
| WO | 2018022146 A1 | 2/2018 | |

OTHER PUBLICATIONS

Search Report received in Chinese Application No. 2019800490980 dated Jun. 29, 2022, with translation, 5 pages.
International Search Report received in Application No. PCT/EP2019/069427 mailed Apr. 22, 2020, 11 pages.
German Search Report received in Application No. 10 2018 130 542.7 dated Mar. 26, 2019, 20 pages.
Written Opinion received in Application No. PCT/EP2019/069427 dated Apr. 22, 2020, 27 pages.

* cited by examiner

MESH TRAY LID FOR MESH STERILIZING TRAY AND MESH STERILIZING TRAY SYSTEM

CROSS-REFERENCE TO RELATED APPLICATIONS

This application is the United States national phase entry of International Application No. PCT/EP2019/069427, filed Jul. 18, 2019, and claims the benefit of priority of German Application No. 10 2018 212 430.2, filed Jul. 25, 2018 and German Application No. 10 2018 130 542.7, filed Nov. 30, 2018. The contents of International Application No. PCT/EP2019/069427, German Application No. 10 2018 212 430.2, and German Application No. 10 2018 130 542.7 are incorporated by reference herein in their entireties.

FIELD

The present invention relates to a mesh tray lid/mesh basket lid/mesh sterilizing basket lid for a mesh sterilizing tray/a sterilizing basket/a sterilizing basket trough/a mesh basket trough/a sterilizing tray, especially having a substantially rectangular plate-like or grid-like basic form which defines an outer/upper side which, when the lid is placed onto the mesh sterilizing tray, faces away from said tray. The invention also relates to a mesh sterilizing tray system comprising a mesh sterilizing tray/a mesh basket trough and a mesh sterilizing lid.

BACKGROUND

In public health care, medical products that come into direct contact with the human body pose a particular risk of infection for the patient. In order to achieve a protection of the patient as efficient as possible against infections by medical products, high demands are made on a hygienic status of the medical products. Concerning critical medical products, sterility is demanded, wherein a sterile medical product is free from organisms capable of reproduction including being free from spores capable of reproduction. For re-use, the products are appropriately purified and sterilized.

Common methods for sterilization are, for example, thermal sterilization methods, either by means of moist heat or by means of hot air, low-temperature gas methods such as ethylene oxide methods, or disinfection methods using aqueous solutions. In said methods, (thermally stable) medical products are disposed in a mesh sterilizing tray/a mesh sterilizing basket/a mesh basket for sterilization and are subjected to the appropriate method.

In order to prevent light or small instruments from being ejected from the mesh sterilizing tray or from inadvertently leaving the tray due to further circumstances, especially during a washing operation, and in order to prevent the medical products from dropping out during transport in sterile barrier systems or on transport wagons, the mesh sterilizing tray is equipped with a dedicated fitting mesh tray lid. Said mesh tray lid closes the mesh sterilizing tray and, due to its geometry, prevents the medical products from exiting the mesh sterilizing tray. In addition, the mesh tray lid may serve for ensuring a clearance between instruments and soft packaging. The mesh tray lid must be locked or closed with the mesh sterilizing tray so as to prevent the mesh tray lid from falling off the mesh sterilizing tray.

As known from the state of the art, in a mesh sterilizing tray system including a mesh sterilizing tray, a mesh tray lid is loosely laid or placed onto the mesh sterilizing tray. After that, two pivoting mesh tray handles or grab handles of the mesh sterilizing tray, which are arranged on two opposite inner side faces of the mesh sterilizing tray and which, while placing the mesh tray lid, were in an upper/remote pivoting position relative to the mesh sterilizing tray (grasping position or carrying position) that enabled the mesh tray lid to be placed, are pivoted downwards to the placed mesh tray lid and finally loosely bear on the mesh tray lid.

However, it is a problem with such a mesh tray lid and, resp., a mesh sterilizing tray system that neither the mesh tray lid nor the mesh sterilizing tray system is adapted to be safely closed, as the mesh tray handles merely rest loosely on the mesh tray lid as a stop. For example, when another mesh sterilizing tray is stacked onto the mesh tray lid, the mesh tray handles can easily be folded or pivoted inadvertently from the bearing position as folded position/closed position into a grasping position which allows the mesh tray lid to be removed from the mesh sterilizing tray. There is also the risk of the content of the mesh sterilizing tray being dumped and becoming unsterile during lifting, if inadvertently only one of the two mesh tray handles is folded and the mesh sterilizing tray system is gripped at the sterilizing lid itself. This may sometimes result in the fact that the required instruments are missing for an operation and such operation may have to be deferred.

In another mesh sterilizing tray system known from the state of the art, a complex closure mechanism comprising a detent hook disposed on the mesh tray lid or on the mesh sterilizing tray and a corresponding engaging mechanism is used which is cost-intensive in manufacture, is susceptible to problems and entails risks in terms of sterilization. Further, from the state of the art a knee lever closure is known which has a C-shaped closure member or closure bracket and can get hooked in a corresponding holding fixture in parallel to the mesh tray lid. However, according to this state of the art, when the mesh tray lid is placed, the mesh tray handles are covered by the same and cannot be manually gripped before the mesh tray lid has been removed. This involves the drawback that the mesh sterilizing tray system therefore always must be lifted and carried by separate carry handles directly on the mesh tray lid so that, on the one hand, the closure mechanism between the mesh tray lid and the mesh sterilizing tray must be construed for the entire weight of the mesh sterilizing tray along with the content, and, on the other hand, further components such as the carry handle have to be fabricated and cleaned.

SUMMARY

Therefore, it is the object of the invention to avoid or at least mitigate the drawbacks known from the state of the art and especially to provide a mesh tray lid and a mesh sterilizing tray system that can be closed easily and safely, is easy to handle, is especially well suited for transport and storage, offers the function that a user can easily handle the mesh tray lid and especially can properly place as well as properly remove the mesh tray lid manually onto or from the mesh sterilizing tray, and to provide a closure or a closure mechanism so as to allow for easy and safe closing by means of a rod-shaped bar member so that especially the mesh tray lid can be safely closed with the mesh sterilizing tray.

As regards the mesh tray lid, the object of the invention thus is achieved, according to the invention, by the fact that the mesh tray lid has such a holding fixture (a detent and/or snap-in device) which is configured so that a rod-shaped bar that is preferably pivoted on the mesh sterilizing tray can be received from a direction substantially perpendicular to the outer side of the mesh tray lid and can be positively and/or frictionally (detachably) connected.

Hence, it is the gist of the present invention to provide such a mesh tray lid which, when it is placed on a mesh sterilizing tray, positively and/or in a force-fit manner receives and detachably fixes/clamps a rod-shaped bar coming from above or from a side facing away from the mesh sterilizing tray.

In accordance with the invention, on the outer side of the mesh tray lid at each of two opposite rim/edge portions, thus a detent and/or snap-in device is formed or arranged which is intended and configured to receive a rod-shaped bar positively and/or in a force-fit manner from a direction substantially perpendicular to the outside.

Solely the design of the mesh tray lid enables the mesh tray lid to be easily and safely closed, especially with a correspondingly fitting mesh sterilizing tray. The mesh tray lid is suited for a rod-shaped bar, such as a bail-like mesh tray handle of the mesh sterilizing tray, being used as part of a lid closure mechanism. A rod-shaped bar/bail handle moving from above onto the mesh tray lid or substantially perpendicularly toward the outer side, which is received by a detent and/or snap-in device, is not known from the state of the art. Such a configuration enables the user to implement a simple and safe closure system outside the mesh tray lid and, resp., the outer side thereof.

Advantageous embodiments are claimed in the dependent claims and are be explained in the following.

In accordance with one embodiment, the detent/latching device and/or snap-in device can be designed to be at least partially, especially completely, elastic so as to receive the rod-shaped bar in a force-fit manner and/or positively by clamping or, resp., to couple and uncouple the same in a force-fit manner and/or positively. The force of the pretension and the internal stress of the elastically configured detent and/or snap-in device is sufficient to receive the rod-shaped bar in a force-fit manner and/or positively by clamping. The force-fit connection is due to a friction force based on the material of the detent and/or snap-in device that contacts the rod-shaped bar. To this end, the detent and/or snap-in device preferably includes two spring tabs or tongues that receive the rod-shaped bar therebetween and, due to the elastic property, press-fit the rod-shaped bar by pressure force exerted on the same. The form closure is due to a geometrical shape of the detent and/or snap-in device, especially an at least partial ( ) or < > overall shape, the elastic property designing the geometrical shape to be variable against its pretension.

According to another aspect of the invention, the detent and/or snap-in device may include an elastic detent portion in the form of an elastic clip/a clip portion/clasp, preferably consisting of the two spring tabs, having a receiving opening oriented substantially perpendicularly to the outer side in which the rod-shaped bar can be engaged against the pretension of the elastic detent portion in at least one position. The clip which protrudes substantially perpendicularly from the outer side and the receiving opening of which faces away from the outer side enables the bar to easily and safely engage in at least one engaging position.

Preferably, at least one of the two detent and/or snap-in devices may include two gripping surfaces facing away from each other which extend substantially perpendicularly to the outer side and, resp., perpendicularly to the substantially rectangular plate-like or grid-like basic form and, thus, allow for gripping of the detent and/or snap-in device according to the pinch grip. Alternatively, or additionally, the detent and/or snap-in device may also include an eyelet or an open or closed bail handle which can be gripped manually, i.e., by the hand/finger by hooking on. Thus, the detent and/or snap-in device is configured to be gripped and to be moved especially in a direction perpendicular to the outer side. The detent and/or snap-in device therefore serves as a mesh tray lid handle so as to be able to place the mesh tray lid preferably onto, as well as to lift the same off, a mesh sterilizing tray.

In accordance with another aspect, the detent and/or snap-in device may include a projection at the edges of each of the two gripping surfaces facing away from each other to form an undercut recessed grip for gripping and pulling in the vertical direction toward the outer side. In this way, a force-fit connection is complemented by a form closure, and the mesh sterilizing lid can be handled even better.

In accordance with another embodiment, the two detent and/or snap-in devices may be identical, especially may be identical separate component parts and may be manufactured in one piece (/integrally) of an elastic material, especially an elastomer. This design allows for inexpensive and simple production, avoids unnecessary undercuts that are difficult to clean and to sterilize, and facilitates a modular kit. Consequently, especially by selecting an appropriate detent and/or snap-in device, the mesh tray lid can be adapted to different mesh sterilizing trays.

Preferably, the mesh tray lid may include, at each of the two opposite edge portions, a recess/cut-out/groove which is preferably substantially rectangular and extends, for example, over about 50% of the total length of the opposite edge portions along the respective edge portion. The recess/cut-out cuts out/leaves uncovered/leaves out an area for an object, especially a mesh tray handle that is mounted on the mesh tray.

Especially, the mesh tray lid may include, in the area of each of the opposite edge portions, an indentation/a trough in a direction perpendicular to the outer side so that a stepping is formed. The recess is especially configured in the indentation. Thus, the indentation attains a stepping of the mesh tray lid into two different height levels of the outer side.

According to one embodiment, the indentation may take a trapezoid shape/may be trapezoidal, with a transition from the indentation to the non-indented outer side having a planar closed surface to stiffen the transition. The trapezoid shape is well suited for receiving different shapes. Especially, the trapezoid shape is suited for current mesh tray handles.

Preferably, the detent and/or snap-in devices may be separate component parts which are fastened positively, especially by means of a snap hook, and/or in a force-fit manner, especially via frictional connection of a plug connection, to the mesh tray lid.

In other words, the invention discloses a mesh tray lid for mesh sterilizing trays (of different form) having at least one rod-shaped bar, in particular in the form of a movable, especially pivotable, mesh tray handle, the mesh tray lid including at least one recess/groove for passing through/for recessing a (respective) mesh tray handle, wherein an indentation for receiving the (respective) mesh tray handle is provided in the mesh tray lid, wherein in the indentation the (respective) recess and an elastic handle holder/an elastic clamping member are provided to detachably fix the (respective) rod-shaped bar, especially the mesh tray handle, in the indentation.

As regards a generic mesh sterilizing tray system comprising a mesh sterilizing tray with at least one movable, especially pivotable, mesh tray handle and a mesh tray lid that can be placed onto the mesh sterilizing tray, the object of the invention is achieved by the fact that preferably a mesh tray lid according to the invention is inserted, and/or that the mesh tray lid includes a detent and/or snap-in device/closure unit/handle holder/clamping member/detent holder (rigidly/tightly) connected/connectable to the mesh tray lid to/into which the mesh tray handle of the mesh sterilizing tray can be connected/coupled/clipped in a force-fit manner and/or positively so as to fix the mesh tray handle in a force-fit manner and/or positively relative to the mesh tray lid in at least one position, especially a pivoting position in parallel to the mesh tray lid, and, in this way, to lock the mesh tray lid relative to the mesh sterilizing tray.

In accordance with the invention, the mesh sterilizing tray system thus provides a system of a mesh sterilizing tray and a mesh tray lid related and adapted to each other in which the mesh tray lid includes a detent and/or snap-in device (clip) in which the mesh tray handle of the mesh sterilizing tray can be detachably received and fixed. The detent and/or snap-in device together with the mesh tray handle forms the closure mechanism of the mesh sterilizing tray system which facilitates safe and easy closing. The mesh tray handle can be moved from a folding position, in which the mesh tray handle is detachably fixed in a force-fit manner and/or positively in the detent and/or snap-in device, to a grasping position, in which the mesh tray handle can be used for carrying, for example.

Preferably, the mesh tray lid may have, at an edge portion, at least one such recess/groove extending (inwards from the outer edge) which is adapted so that it recesses the mesh tray handle pivoted into the grasping position, when the mesh tray lid is placed. Hence, the recess is configured so that it recesses the respective mesh tray handle so that, for example in a mesh sterilizing tray having two opposite inside mesh tray handles, the mesh tray lid can be received, when the mesh tray handles are erected (grasping/unfolding position), between said two handles and can finally be placed on the mesh sterilizing tray.

According to another aspect of the invention, in the mesh tray lid at least one indentation/trough can be provided which is adapted to receive the at least one mesh tray handle of the mesh sterilizing tray, and in the indentation (indented portion) preferably the recess and the detent and/or snap-in device can be disposed to detachably fix the mesh tray handle in the indentation. Thus, the indentation has such a shape that the mesh tray handle can be inserted or received in the indentation. In this way, the mesh tray handle can be disposed, in a folding position in which the mesh tray lid is closed or locked with the mesh sterilizing tray, beneath or flush with the height of the remaining outer side of the mesh tray lid so that, during stacking, the lid does no longer form the highest or outermost point of the mesh sterilizing tray system, and the mesh sterilizing trays thus can easily be stacked.

Preferably, each of the detent and/or snap-in devices may have an elastic detent portion in the form of an elastic clip or a clip portion (two-armed clip) in which the mesh tray handle can be engaged against the pretension of the elastic detent portion in at least one position. The detent and/or snap-in device of the mesh tray lid and the mesh tray handle are adapted or adaptable to each other as to their relative position such that the mesh tray handle forms the rod-shaped bar and, when the latter is pivoted, can be received positively and/or in a force-fit manner by the detent and/or snap-in device.

BRIEF DESCRIPTION OF THE DRAWING FIGURES

Figure 2:
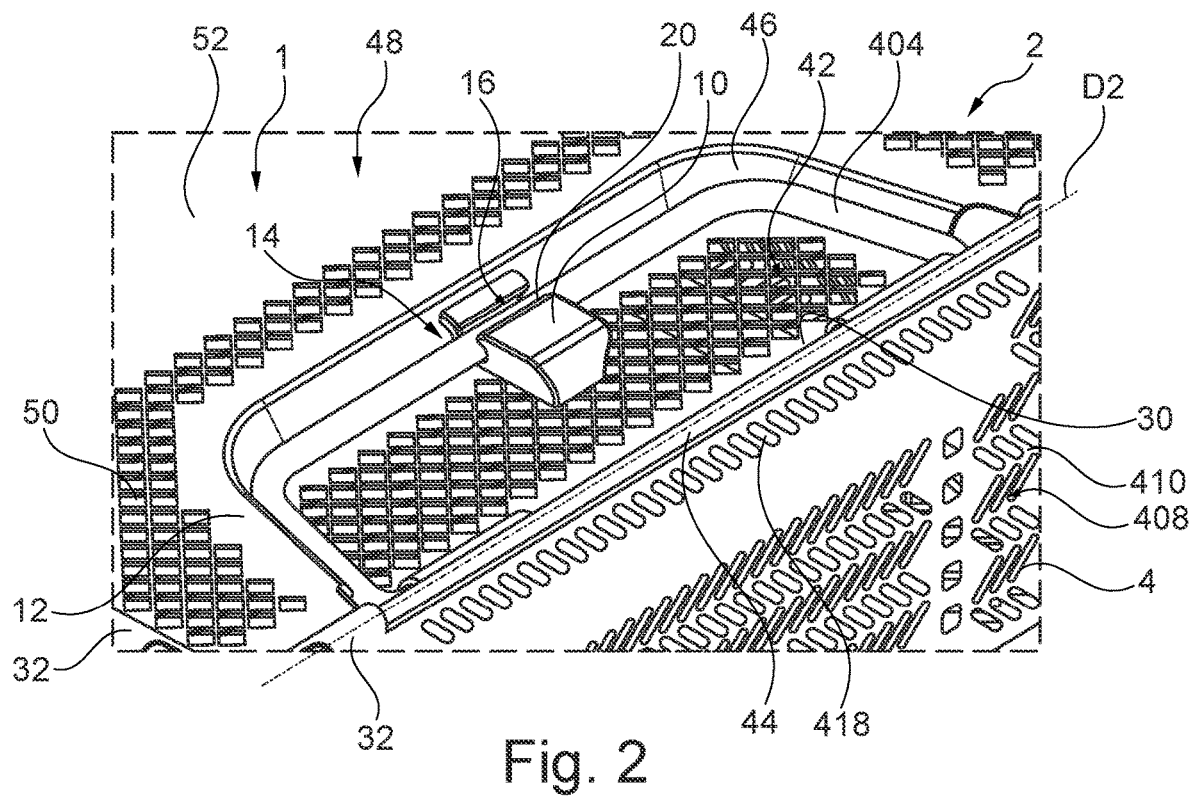
Figure 3:
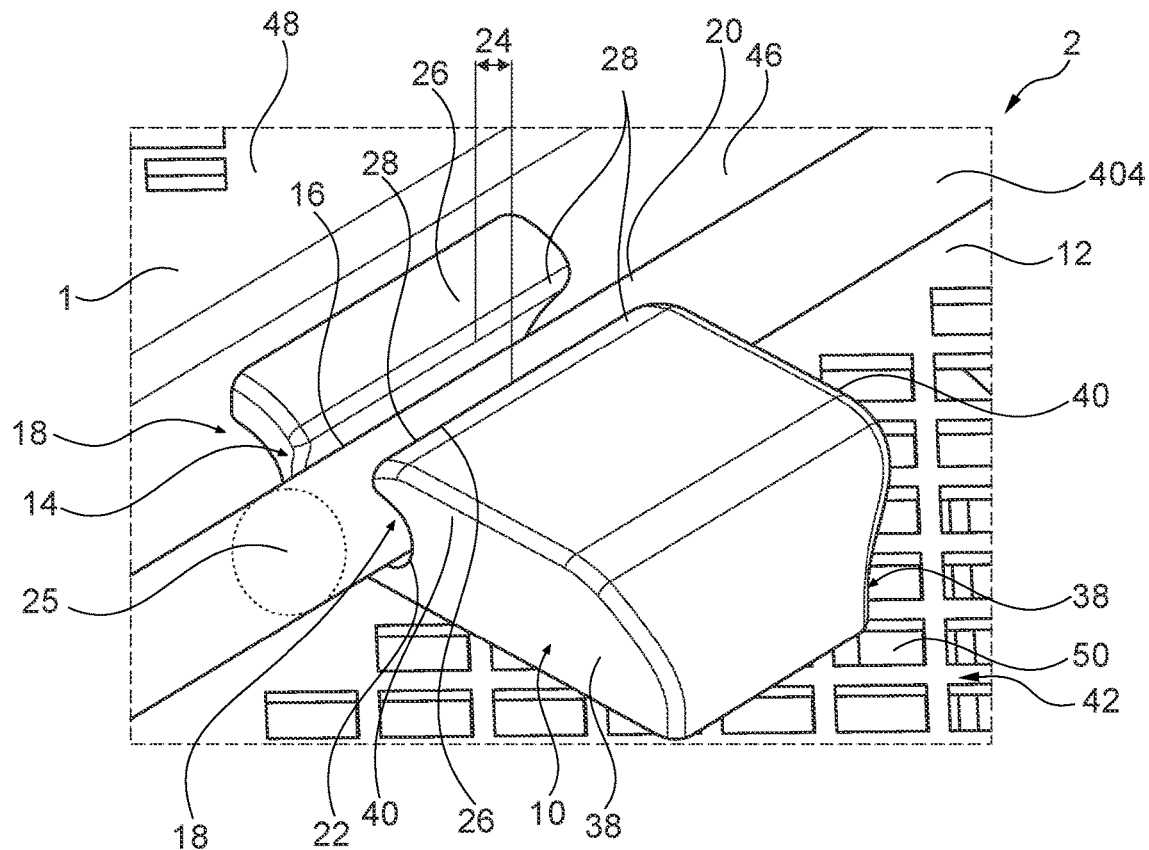
Figure 4:
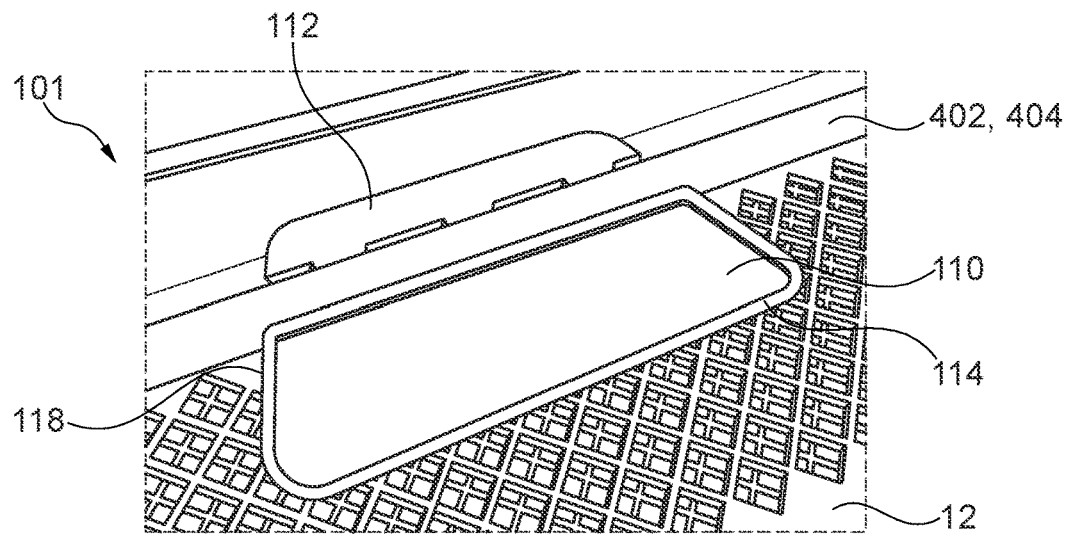
Figure 5:
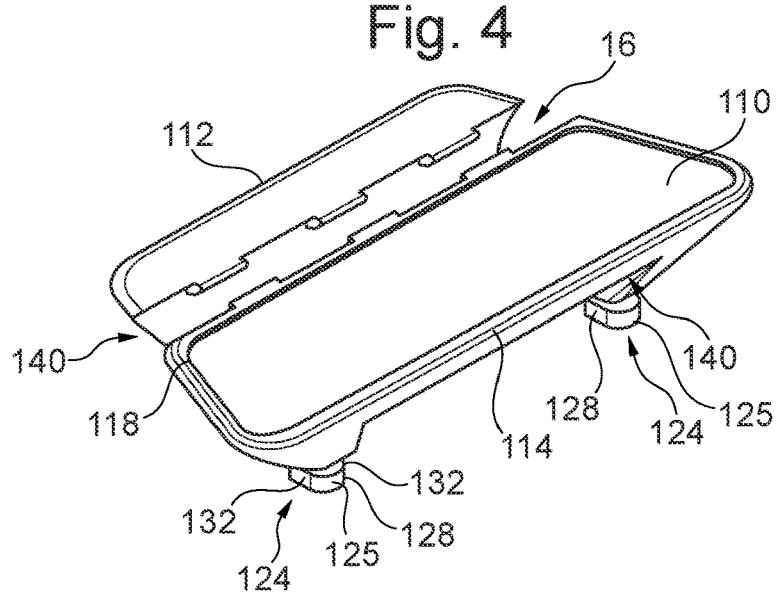
Figure 6:
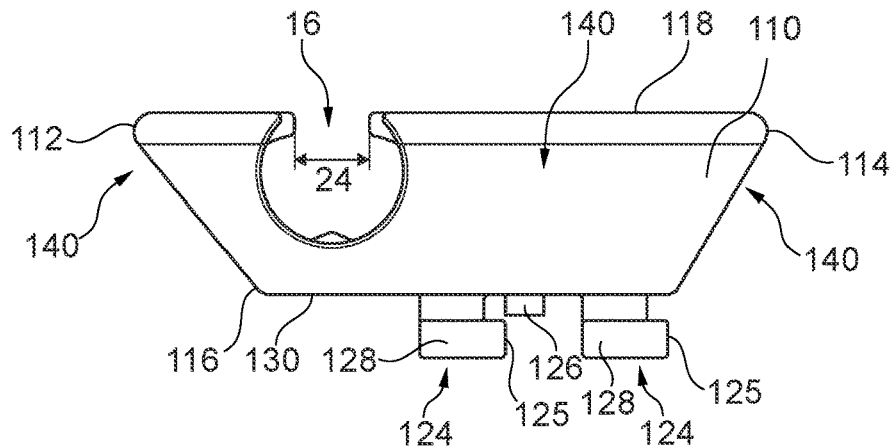

Hereinafter, the present invention shall be illustrated in detail by means of preferred embodiments with reference to the accompanying figures, wherein:

FIG. 1 shows a perspective view of a mesh tray lid according to the invention as set forth in a preferred embodiment which is inserted in a mesh sterilizing tray system according to the invention as set forth in a preferred embodiment, FIGS. 2 and 3 show detailed perspective partial views from FIG. 1, FIG. 4 shows a perspective partial view of a mesh tray lid according to the invention of another preferred embodiment, FIG. 5 shows a perspective view of a detent and/or snap-in device of the mesh tray lid from FIG. 4, and FIG. 6 shows a side view of the detent and snap-in device from FIG. 4 and FIG. 5.

The figures are schematic and are intended to serve only for the comprehension of the invention. The same elements are provided with the same reference numerals. The features of the different embodiments can be interchanged.

DETAILED DESCRIPTION

FIGS. 1 to 3 illustrate a mesh sterilizing tray system 2 according to the invention as set forth in a preferred embodiment comprising a mesh sterilizing tray 4 and comprising an already placed mesh tray lid 1 according to the invention as set forth in a preferred embodiment at the two opposite rim/edge portions 6, 8 of which a respective detent and/or snap-in device 10 (as closure unit) is disposed, the latter being positioned or positionable at the mesh tray lid 1 so that a mesh tray handle 402, 404 hinged to the mesh sterilizing tray 4 can engage, when the handle is pivoted, in the detent and/or snap-in device 10 like a rod-shaped bar and, thus, can secure the mesh tray lid 1 on the mesh sterilizing tray 4. The mesh tray lid 1 placed on the mesh sterilizing tray 4 defines an outer surface 12 that faces away from the mesh sterilizing tray 4.

The detent and/or snap-in device 10 is configured so that it can receive the bail-type mesh tray handles 402, 404 of the mesh sterilizing tray 4, shaped in the form of a curved rod each from a direction substantially perpendicular to the outer side 12 of the mesh tray lid 1, in a force-fit manner and positively and couple or clip them by clamping. For this purpose, each of the two detent and/or snap-in devices 10 includes an elastically configured clip-type detent and snap-in portion or a clip portion 14, the receiving opening 16 of which is oriented, for receiving the mesh tray handles 402, 404, to project perpendicularly from the outer side 12. The clip portion 14 includes two opposite spring tabs 18 so as to receive and press-fit the mesh tray handle 402, 404 or a rod-shaped bar or rod-shaped bar portion 20 of the mesh tray handles 402, 404 therebetween, and, in this way, to receive it in a force-fit manner and positively and to couple it by clamping.

The function of securing the mesh sterilizing tray system 2 and the interaction between the mesh tray lid 1 according to the invention and the mesh sterilizing tray 4 shall be explained hereinafter with a detailed description of the detent and/or snap-in device 10 and the mesh sterilizing tray 4 comprising the mesh tray handles 402, 404.

The clip portion 14 of the detent and/or snap-in device 10 includes, situated between the two spring tabs 18, a respective receiving channel 22 in which the respective received rod-shaped bar portion 20 of the mesh tray handles 402, 404 can be positively received. Accordingly, a direction of the longitudinal axis L of the receiving channel 22 is both parallel to the edge portions 6, 8 and, with the mesh tray lid 1 being placed, parallel to the rod-shaped bar portions 20 of the mesh tray handles 402, 404. When the mesh tray handles 402, 404 are pivoted to a folding position and engage in the detent and/or snap-in device 10, the rod-shaped bar portion 20 of the mesh tray handles 402, 404 is finally coaxial to the direction of the longitudinal axis L of the receiving channel 22. The receiving opening 16 of the receiving channel 22 is in the form of a receiving slit and, along its extension, has a constant opening width 24 that is (slightly) smaller than both a diameter of the receiving channel 22 and a diameter 25 of the rod-shaped bar 20 of the mesh tray handles 402, 404. The constriction causes two opposite detent lugs or detent projections 26 to be formed in the clip portion 14 of the detent and snap-in device 10.

The two detent and snap-in devices 10 are identically configured and are made in one piece/integrally from a material of defined inherent elasticity. In particular, the material of the detent and snap-in device 10 is a sterilizable and heat-resistant elastomer. The detent and snap-in device 10 and, thus, also the clip portion 14 is rendered elastic by the elastomer so that the two opposite detent projections 26 of the clip portion 14 can be pushed apart against their pretension caused by an elastic deformation. The term 'elastic' in this context means that the material has such an elasticity that the detent projections 26 of the clip portion 14 can be manually pushed apart so that the opening width 24 may temporarily adopt the diameter of the receiving channel 22 or, resp., the diameter 25 of the rod-shaped bar 20 and the constriction is temporarily cancelled. In order to allow the mesh tray handles 402, 404 to couple and uncouple or, resp., to engage and disengage even better in and from the detent and snap-in device 10, the detent projections 26 include a respective ramp/ramp structure 28 on both their side facing away from the outer side 12 and their side facing the outer side 12.

However, each of the bail-type mesh tray handles 402, 404 is hinged, rotatably or pivotally about an axis of rotation D1, D2, at the inside or at the tray inside to two opposite short side faces 410 of a circumferential wall 408 of the mesh sterilizing tray 4 that extends perpendicularly to a bottom surface 406. Each of the axes of rotation D1, D2 is in parallel to the short side face 410. The bail-type mesh tray handles 402, 404 may be pivoted about their axes of rotation D1, D2, starting from a grasping/unfolding position pointing substantially vertically upwards, inwards into the mesh sterilizing tray 4 or vice versa. The bail-type mesh tray handles 402, 404 are articulated to an upper portion, when viewed in FIG. 1, of the short side faces 410 that faces away from the bottom surface 406.

When the two mesh tray handles 402, 404 are positioned in a grasping position, the mesh tray lid 1 can be placed onto the mesh sterilizing tray 4, wherein the two mesh tray handles 402, 404 can further be (manually) reached from outside, even after the lid has been placed. For this purpose, the mesh tray lid 1 includes, at each of the two opposite edge portions 6, 8, a recess/groove 30 that extends along the edge portions 6, 8. The recesses 30 of the mesh tray lid 1 are configured such that they recess the mesh tray handles 402, 404. In this way, the mesh tray lid 1 can be inserted between the mesh tray handles 402, 404 in the grasping position.

At each of its four edges, the mesh tray lid 1 has an (inverted) collar/attaching channel 32 that projects from the outer side 12 and, resp., from the edges of the mesh tray lid 1 toward the mesh sterilizing tray 4. The collars 32 are made by means of a bending process as a re-forming process. At two long edges 34 of the mesh tray lid 1 having a substantially rectangular basic form, the collar 32 extends almost entirely along the edge 34. At two short edges 36 of the mesh tray lid 1 which also constitute the edge portion 6, 8, the collar 32 is formed outside the area of the mesh tray handles 402, 404. All of the collars 32 are located at the same height and, resp., in a common plane.

When the mesh tray lid 1 is placed onto the mesh sterilizing tray 4, the collar 32 encompasses an upper peripheral rim 414 of the circumferential wall 408. Thus, the mesh tray lid 1 is positively fixed and merely has a degree of freedom perpendicularly to the outer side 12 and, resp., in the vertical direction in order to lift the mesh tray lid 1 off the mesh sterilizing tray 4 again.

When the two mesh tray handles 402, 404 are pivoted, starting from the grasping position, about their axes of rotation D1, D2 inwards into the sterilizing tray 4, they rest exactly on the receiving opening 16 symmetrically between the two detent projections 26, due to the detent and snap-in device 10 adapted to the mesh tray handles 402, 404 and a fitting arrangement/positioning relative to each other. A central handle portion 416 of the mesh tray handles 402, 404 which extends in parallel to the axis of rotation D1, D2 and is rod-shaped constitutes the rod-shaped bar portion 20 of the mesh tray handles 402, 404. When the two mesh tray handles 402, 404 are pivoted further inwards, or when compressive force is applied to the mesh tray handles 402, 404 perpendicularly onto the outer side 12 of the mesh tray lid 1, the mesh tray handles 402, 404 engage in the clip portion 14. Hence, compressive force on the mesh tray handles 402, 404 is continued to be increased in the direction perpendicular to the outer side 12, until the rod-shaped bar portion 20 has pushed the two detent projections 26 of the receiving opening 16 elastically apart by means of the ramp structure 28 so that the opening width 24 temporarily corresponds to the diameter 25 of the rod-shaped bar 20 and thereafter engages and snaps in the receiving channel 22 positively and in a force-fit manner.

When the mesh tray handles 402, 404 are finally received positively and in a force-fit manner in the respective detent and snap-in device 10 as a closure unit, the mesh tray handles 402, 404 together with the detent and snap-in devices 10 realize a closure of the mesh tray lid 1 with the mesh sterilizing tray 4 and, resp., a closure of the mesh sterilizing tray system 2. The mesh tray handles 402, 404 are in a folding position and the mesh tray lid 1 can no longer be removed from the mesh sterilizing tray 4.

Analogously to the foregoing procedure, the mesh tray handles 402, 404 can be disengaged or uncoupled again. To this end, the mesh tray handles 402, 404 are forced or pressed substantially perpendicularly (upward) away from the outer side 12, wherein the two detent projections 26 are forced apart by means of the ramp structure 28 again.

When the mesh sterilizing tray 4 is to be carried by hand, the two mesh tray handles 402, 404 can be manually disengaged, and the mesh sterilizing tray 4 can be carried together with the mesh tray lid 1 by means of the mesh tray handles 402, 404. In so doing, the mesh tray handles 402, 404 act directly upon the mesh sterilizing tray 4 so that, in contrast to the state of the art, inadvertent release of the mesh tray lid 1 will not result in the entire content of the mesh sterilizing tray 4 falling out.

In the mesh sterilizing tray system 2, closing of the mesh tray lid 1 on the mesh sterilizing tray 4 is performed by engaging the mesh tray handles 402, 404 in the detent and snap-in device 10 and enables easy and safe closing, wherein the closure concept enables the mesh sterilizing tray 4 to be carried at the mesh tray handles 402, 404, and carrying at the mesh tray lid 1 is not required.

For manually placing and removing the mesh tray lid 1, the detent and snap-in device 10 includes two grip surfaces 38 facing away from each other which are preferably configured in parallel to each other and thus project substantially perpendicularly from the outer side 12. Said grip surfaces 38 serve for manual gripping and handling of the detent and snap-in device 10 and thus for gripping and handling of the mesh tray lid 1. In order to further assist manual gripping at the detent and snap-in device 10, (rounded) projections 40 are provided at upper edges of the grip surfaces 38 so that the mesh tray lid 1 can be handled not only by means of force closure or frictional connection but also by means of form closure.

In the area of the edge portions 6, 8, the mesh tray lid 1 further includes an indentation or a trough 42 in a direction perpendicular to the outer surface 12. The surface of the indentation 42 is parallel to the remaining non-indented surface of the mesh tray lid 1 so that a kind of step or stepping forms in the mesh tray lid 1. The entire mesh lid 1 as well as the two opposite indentations 42 are formed to be symmetrical to a first plane of symmetry E1. Also, the entire mesh lid 1 and thus also the two indentations 42 are formed to be symmetrical to a second plane of symmetry E2. The two planes of symmetry E1 and E2 are orthogonal to each other. The indentation 42 has an isosceles trapezoidal contour/shape, with a long base side 44 of the trapezoidal contour forming the respective opposite edge portions 6, 8. At the remaining three sides of the trapezoidal contour of the indentation 42, the latter includes a transition 46 to the non-indented area of the mesh tray lid 1. Said transition 46 from the trapezoidal indentation 42 to the (remaining) outer side 12 has a planar closed surface to stiffen the transition 46. Both the transition 46 and the indentation 42 were reshaped by means of deep-drawing.

Analogously, also the mesh tray handles 402, 404 show a corresponding trapezoidal shape so that, in the folding position, they are received in the corresponding trapezoidal indentation 42. Then they are substantially in parallel to the bottom surface 406 of the mesh sterilizing tray 4. The indentation 42 allows to properly stack several sterile container systems 2 on top of each other.

The mesh tray lid 1 has a substantially rectangular grid-like basic form as a sheet metal lid 48 made from aluminum or stainless steel which, when placed on the mesh sterilizing tray 4, defines the outer side 12 which in this embodiment is substantially planar or uncurved, apart from the transition 46, and which faces away from the mesh sterilizing tray 4. In the sheet metal lid 48 a plurality of square openings 50 is punched out to provide a fluid communication between an inner side and the outer side 12 and thus to render the outer side 12 especially penetrable by steam. A central lid area 52 of the mesh tray lid 1 or of the sheet metal lid 48 is closed in plate shape, on the other hand, and merely in the center thereof includes a number of, preferably five, square punched-out openings 50. The structure of the mesh tray lid 1 is stiffened by the plate-shaped central area 12. Alternatively, the central lid area 52 may have a perforation, especially a plurality of punched-out openings 50.

The mesh sterilizing tray 4 of the mesh sterilizing tray system 2 also includes the substantially rectangular mesh-like or grid-like bottom surface 406 as well as the mesh-like circumferential wall 408 of equal height that extends around the circumference of the bottom surface 406 and is perpendicular to the bottom surface 406. The bottom surface 406 and the circumferential wall 408 together form the shell- or trough-shaped configuration. Both the bottom surface 406 and the circumferential wall 408 include a plurality of openings 418 in the form of longitudinal slits so as to be (fluid) permeable to especially hot steam and, resp., to moist hot air. The material of the bottom surface 406 and the circumferential wall 408 is aluminum or stainless steel.

Furthermore, the mesh sterilizing tray 4 includes, at its long side faces 412, webs 420 from the bottom surface 406 to the peripheral edge 414 to reinforce and stiffen the long side faces 412. Moreover, in a central sidewall area 422 of the long side face 412 a closed sheet metal surface is provided for stiffening. As an alternative, the central sidewall area 422 may also be designed perforated with punched-out slotted openings 418 so that an even better fluid communication is achieved.

FIGS. 4 to 6 illustrate a mesh tray lid 101 according to the invention of another second preferred embodiment comprising a fastened detent and snap-in device 110. The mesh tray lid 101 is identical to the mesh tray lid 1 of the first embodiment, apart from the differently designed detent and snap-in device 110; therefore, in the following merely the detent and snap-in device 110 will be described and, regarding the further features of the mesh tray lid 101, it is referred to the foregoing description.

The detent and snap-in device 110 illustrated in FIGS. 4 to 6 in this embodiment in a top view (view onto the detent and snap-in device 110 and, resp., onto the mesh tray lid 101) has a (contour) shape of an isosceles symmetrical trapezoid with a parallel short base side 112 and a long base side 114. The long base side 114 faces the respective edge portion 6, 8 of the mesh tray lid. In the same way, in a side view (see FIG. 6), the detent and snap-in device 110 has a (contour) shape of an isosceles and symmetrical trapezoid whose lower base side 116 rests on and, resp., faces the mesh tray lid 101, and whose upper base side 118 includes the receiving opening 16 with the opening width 24 and faces away from the short base side 12. In a front view of the detent and snap-in device 110, too, the same has a (contour) shape of an isosceles symmetrical trapezoid whose short base side faces the short base side 12, thereby on the whole a segment/portion of a pyramid of trapezoidal base area being formed whose imaginary tip is located on the opposite side of the short base side 12 and in (the direction of) the mesh sterilizing tray 4, when the mesh tray lid 101 is placed. By the geometrical shape of the detent and snap-in device 110, grip projections 140 for improved manual gripping and handling of the detent and snap-in device 110 are formed on all four sides.

Arranged in parallel to as well as between the short and long base sides 112, 114, there extends the receiving channel 22 which can receive the mesh tray handles 402, 404. The detent and snap-in device 110 further includes, for connecting the mesh tray handles 402, 404, three opposite (rounded) tensioning projections/tensioning tongues 120 arranged along the longitudinal axis L of the receiving channel 22 and in the area of the receiving opening 16. The tensioning projections 120 protrude, as is also evident from FIG. 6, into the receiving channel 22 formed to be (semi)circular when viewed in cross-section at the open or upper side thereof and thus narrow the semi-circularly configured receiving channel 22 on the side of the receiving opening 16. The semi-circular contour of the receiving channel 22 is dented by the tensioning projections 120 so that a mushroom-shaped or bollard-shaped cross-sectional contour is resulting. In the same way, in the center of the receiving channel 22 an elevation 122 is provided in the direction of the receiving opening 16 so that, when viewed in the side view in FIG. 6, a shape of a locking plate having three projections toward the longitudinal axis L is formed. When the mesh tray handles 402, 404 are grasped, the tensioning projections 120 appropriately pretension the mesh tray handles while interacting with the elevation 122 so that the mesh tray handles 402, 404 are safely held in the receiving channel and do not wobble or rattle.

The detent and snap-in device 110 includes four feet 124 and a locking projection 126 for being fastened to the mesh tray lid 101. Two out of the four feet 124 at a time are located on a parallel to the short and, resp., long base sides 112, 114. All of the four feet 124 (see especially FIG. 6. Are L-shaped and extend away from a lower side of the detent and snap-in device 110. A tip or an end 125 of each of the L-shaped feet 124 points to the same direction, namely to the long base side 114 of the detent and snap-in device 110 (and, consequently, transversely to the longitudinal axis L). A lower portion 128 of the L shape that is located in parallel to the lower base side 116 and to a bearing surface 130 of the detent and snap-in device 110 on the mesh tray lid 101 is plate-shaped and includes foot projections 132 in the direction of the longitudinal axis L so that, in a front view, the foot 124 has a T-profile and an undercut is formed to both sides in the direction of the longitudinal axis L. The tip 125 of the L-shaped feet 124 is rounded toward the two foot projections 132. The feet 124 are adapted to the openings 50 of the mesh tray lid 101 so that all of the four feet can be inserted initially perpendicularly into the openings 50 of the mesh tray lid 1 so that the bearing surface 130 rests directly on the outer face 12. Hereafter, the detent and snap-in device 110 is displaced in the direction of the long base side 114 so that the L shape of the feet 124 with an undercut positively moves beneath braces of the grid structure of the openings 50. A distance between the bearing surface 130 and the plate-shaped lower portion 128 corresponds to the thickness of the grid structure of the openings 50. Hereafter, the detent and snap-in device 110 is locked at the mesh tray lid 101 in the direction perpendicular to the outer side 12 and can be removed from the grid structure again only when the L-shaped feet 124 are pushed back. The locking projection 126 is used when interacting with one of the openings 50 into which it projects and on the sides of the grid structure of which it abuts by form closure, for the fact that the detent and snap-in device 110 and, resp., the feet 124 thereof can no longer be displaced in the plane of the bearing surface 130, and, thus, the detent and snap-in device 110 is safely fastened to the mesh tray lid 101. Apart from the locking portion 126, moreover a grasped mesh tray handle 402, 404 prevents the detent and snap-in device 101 from moving toward the short base side 112 and an undercut of the plate-shaped portion 128 and, resp., of the L-shaped feet 124 with the mesh tray lid 101 from being cancelled.

The detent and snap-in device 110 is formed in one part from an elastic material so that with manual force, on the one hand, the mesh tray handles 402, 404 can be engaged and disengaged and, on the other hand, the locking projection 126 can be hooked in and unhooked by elastic deformation. In this way, the detent and snap-in device 110, corresponding to the mesh tray handles 402, 404, can be arranged, positioned, replaced in the openings 50 and can also be removed from the same again without the use of tools.

The invention claimed is:

1. A mesh sterilizing tray system comprising:
    a mesh sterilizing tray; and
    a mesh tray lid,
    the mesh sterilizing tray having at least one mesh tray handle that is movable,
    the mesh tray lid comprising at least one detent and/or snap-in device, the mesh tray lid being configured to be placed onto the mesh sterilizing tray,
    the at least one mesh tray handle having a rod-shaped bar portion and being configured to be coupled in a force-fit manner and/or positively so as to fix the at least one mesh tray handle relative to the mesh tray lid in a force-fit manner and/or positively to the at least one detent and/or snap-in device of the mesh tray lid in at least one position and thus to lock the mesh tray lid relative to the mesh sterilizing tray,
    the mesh tray lid having a substantially rectangular plate-like or grid-like form that defines an outer side that faces away from the mesh sterilizing tray when being placed onto the mesh sterilizing tray,
    the at least one detent and/or snap-in device, which is configured for receiving the rod-shaped bar portion positively and/or in a force-fit manner from a direction substantially perpendicular to the outer side, is formed or arranged on at least one edge portion on the outer side of the mesh tray lid,
    wherein the at least one detent and/or snap-in device comprises an elastic detent portion comprising an elastic clip in which the at least one mesh tray handle is configured to be engaged in at least one position against a pretension of the elastic detent portion.

2. The mesh sterilizing tray system according to claim 1, wherein the mesh tray lid includes, at the at least one edge portion, at least one cut-out which is adapted such that, when the mesh tray lid is placed, the mesh tray lid leaves the at least one mesh tray handle uncovered when the at least one mesh tray handle is pivoted to a grasping position.

3. The mesh sterilizing tray system according to claim 2, wherein, in the mesh tray lid, an indentation is provided which is adapted for receiving the at least one mesh tray handle.

4. The mesh sterilizing tray system according to claim 1, wherein the at least one detent and/or snap-in device is formed to be elastic in order to receive the rod-shaped bar portion of the at least one mesh tray handle in a force-fit manner and/or positively by clamping.

5. The mesh sterilizing tray system according to claim 1, wherein the at least one detent and/or snap-in device comprises an elastic detent portion formed as an elastic clip having a receiving opening oriented substantially perpendicularly to the outer side, wherein the rod-shaped bar portion of the at least one mesh tray handle is adapted to be engaged in the receiving opening in at least one position against a pretension of the elastic detent portion.

6. The mesh sterilizing tray system according to claim 1, wherein the at least one detent and/or snap-in device comprises two detent and/or snap-in devices, at least one of the two detent and/or snap-in devices comprising
    gripping surfaces facing away from each other that extend substantially perpendicularly to the outer side.

7. The mesh sterilizing tray system according to claim 6, wherein each gripping surface comprises
    a projection at an edge of said gripping surface, wherein the projections of the gripping surfaces face away from each other so as to form an undercut recessed grip for gripping and pulling in a direction perpendicular to the outer side.

8. The mesh sterilizing tray system according to claim 6, wherein the two detent and/or snap-in devices are identically formed component parts, and are made in one piece from an elastic material.

9. The mesh sterilizing tray system according to claim 1, wherein the at least one edge portion comprises a first edge portion and a second edge portion opposite the first edge portion, and the mesh tray lid includes, at each of the first and second edge portions, a cut-out which is formed to be substantially rectangular.

10. A mesh sterilizing tray system comprising a mesh sterilizing tray having at least one mesh tray handle having a rod-shaped bar portion that is movable and a mesh tray lid configured to be placed onto the mesh sterilizing tray, wherein the mesh tray lid includes a detent and/or snap-in device connected to the mesh tray lid, the detent and/or snap-in device being elastic to receive the rod-shaped bar portion of the at least one mesh tray handle of the mesh sterilizing tray in a force-fit manner and/or positively so as to fix the at least one mesh tray handle relative to the mesh tray lid frictionally and/or positively in at least one position and thus to lock the mesh tray lid relative to the mesh sterilizing tray.

11. A mesh sterilizing tray system comprising:
a mesh sterilizing tray; and
a mesh tray lid,
the mesh sterilizing tray having at least one mesh tray handle that is movable,
the mesh tray lid comprising at least one detent and/or snap-in device, the mesh tray lid being configured to be placed onto the mesh sterilizing tray,
the at least one mesh tray handle having a rod-shaped bar portion and being configured to be coupled in a force-fit manner and/or positively so as to fix the at least one mesh tray handle relative to the mesh tray lid in a force-fit manner and/or positively to the at least one detent and/or snap-in device of the mesh tray lid in at least one position and thus to lock the mesh tray lid relative to the mesh sterilizing tray,
the mesh tray lid having a substantially rectangular plate-like or grid-like form that defines an outer side that faces away from the mesh sterilizing tray when being placed onto the mesh sterilizing tray,
the at least one detent and/or snap-in device, which is configured for receiving the rod-shaped bar portion positively and/or in a force-fit manner from a direction substantially perpendicular to the outer side, is formed or arranged on at least one edge portion on the outer side of the mesh tray lid,
the at least one detent and/or snap-in device comprising two detent and/or snap-in devices, and
the two detent and/or snap-in devices being identically formed component parts and made in one piece from an elastic material.

* * * * *